United States Patent
Ficini et al.

[11] 4,245,112
[45] Jan. 13, 1981

[54] NOVEL PENTEN-2-YL-DERIVATIVES

[75] Inventors: Jacqueline Ficini, Paris; Jean-Pierre Genet, Fontenay aux Roses, both of France

[73] Assignee: Roussel Uclaf, Paris, France

[21] Appl. No.: 97,709

[22] Filed: Nov. 27, 1979

[30] Foreign Application Priority Data

Dec. 13, 1978 [FR] France ............... 78 35047

[51] Int. Cl.³ .................................. C07C 69/732
[52] U.S. Cl. .................................. 560/181
[58] Field of Search ................. 560/181, 183, 185

[56] References Cited

U.S. PATENT DOCUMENTS 3,558,659  1/1971  Julia ..................... 560/124

FOREIGN PATENT DOCUMENTS 51-1082242  7/1976  Japan ..................... 560/124

*Primary Examiner*—Natalie Trousof
*Assistant Examiner*—L. Hendriksen
*Attorney, Agent, or Firm*—Hammond & Littell, Weissenberger and Muserlian

[57] ABSTRACT

Novel penten-2-yl derivatives of the formula in the trans form

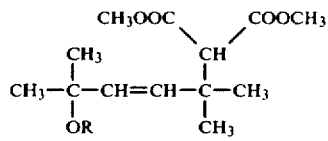

wherein R is selected from the group consisting of hydrogen and acetyl and to a novel process for the preparation of methyl 2,2-dimethyl-3-(2'-methyl-propenyl)-cyclopropane-1,1-dicarboxylate which is an intermediate for chrysanthemic acid.

3 Claims, No Drawings

NOVEL PENTEN-2-YL-DERIVATIVES

STATE OF THE ART

Japanese patent application Ser. No. 75-089508 describes the cyclization of halogenated ethylenic esters in the presence of a base but not a palladium complex.

OBJECTS OF THE INVENTION

It is an object of the invention to provide the novel compounds of formula I and to provide a novel process for their preparation.

It is another object of the invention to provide a novel process for the preparation of methyl 2,2-dimethyl-3-(2'-methyl-propenyl)-cyclopropane-1,1-dicarboxylate.

These and other objects and advantages of the invention will become obvious from the following detailed description.

THE INVENTION

The novel compounds of the invention are penten-2-yl derivatives of the formula in the trans form

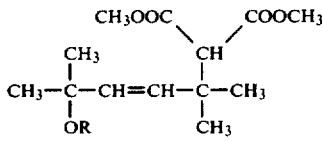

wherein R is selected from the group consisting of hydrogen and acetyl. Preferred compounds of formula I are methyl trans (4-hydroxyl-1,1,4-trimethyl-pent-2-enyl)-propanedioate and methyl trans (4-acetyloxy-1,1,4-trimethyl-pent-2-enyl)-propanedioate.

The novel process of the invention for the preparation of a compound of formula I comprises reacting a cis compound of the formula

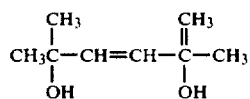

with an acetylation agent to obtain a monoacetate of cis form of the formula

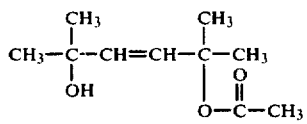

reacting the latter with a sodium malonate derivative of the formula

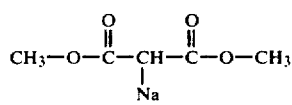

in the presence of a palladium (o) complex in an organic solvent to obtain a compound of the formula in the trans form

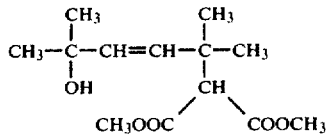

and optionally reacting the latter with an acetylation agent to obtain a compound of the formula in the trans form

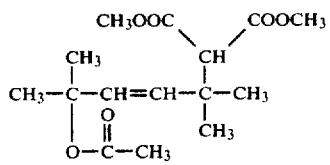

In a preferred mode of the said process, the monoacetylation of the compounds of formulae II and IA is effected with acetic acid anhydride in the presence of triethylamine and a catalytic amount of 4-(N,N-dimethylamino)-pyridine and the palladium (o) complex is preferably palladium tetrakistriphenyl phosphine. The yields of the process are excellent and it begins with a starting material which is chemically simple and inexpensive.

The use of palladium derivatives in the substitution of allylic acetates is a method only known to be in the case of monofunctional acetates [J. Org. Chem., Vol. 41 (1976), p. 3216]. The advantage of the process of the invention essentially resides in the fact that the acetate function is not removed due to the presence of palladium, the malonate group is regio selectively introduced and that the reaction is stereoselective permitting isomerization of the cis form to the desired trans form. The use of a palladium derivative which complexes the double bond permits the production of only the trans form.

The compounds of formula I are intermediates for the synthesis of chrysanthemic acid by allowing the production of methyl 2,2-dimethyl-3-(2'-methyl-propenyl)-cyclopropane-1,1-dicarboxylate which has the formula

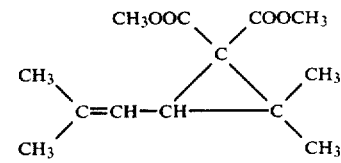

The said compound is described in Bull. Soc. Chim. Japan, Vol. 50 (10) (1977) p. 2825-2826 and may be reacted with lithium chloride in dimethylsulfoxide in the presence of water as described in J. Org. Chem., Vol. 43 (1978), p. 138 to form the corresponding methyl monoester which may be epimerized in a strong base such as sodium ethylate in ethanol as described in Bull. Soc. Chim. of France, (1966), p. 3499 to obtain methyl trans chrysanthemate which may be saponified to trans chrysanthemic acid.

The novel process of the invention for the preparation of methyl 2,2-dimethyl-3-(2'-methyl-propenyl)-cyclopropane-1,1-dicarboxylate comprises reacting the compound of formula I wherein R is acetyl with an alkali metal hydride in an organic solvent and then with a palladium (o) complex to obtain the said desired compound.

In a preferred embodiment of the said process, sodium hydride in a mixture of tetrahydrofuran and hexamethylphosphorotriamide is used and the reaction mixture is poured into a solution of palladium tetrakis-triphenyl phosphine in a mixture of the same solvents.

The said process may also begin with the compound of formula I wherein R is hydrogen if in the first step the said compound is acetylated to form the corresponding monoacetate derivative which is then reacted as before.

The interest in the use of a palladium derivative for the cyclization step proceeds from the fact that the reaction which is regioselective is accelerated in the presence of palladium leading in effect under good conditions by attacking the less blocked pole of the formed complex to the desired structure.

Finally, the invention permits one to proceed to the trans chrysanthemic structure, especially methyl trans chrysanthemate in a novel way with a reduced number of steps beginning with a readily available hex-2-ene derivative.

The compounds of formulae I and V are obtained under perfectly reproducible conditions with interesting total yields. The compound of formula V is known in the literature and can produce in 2 steps methyl trans chrysanthemate in excellent yields.

The compound of formula II is described in J. Org. Chem. Vol. 27 (1962), p. 2398 and C.A., Vol. 59, p. 2675a and C.A. Vol. 85 (1976), p. 76937 m.

In the following examples there are described several preferred embodiments to illustrate the invention. However, it is to be understood that the invention is not intended to be limited to the specific examples.

EXAMPLE 1

Methyl trans (4-hydroxy-1,1,4-trimethyl-pent-2-enyl)-propane-dioate

STEP A: cis 2,5-dimethyl-hex-3-ene-2,5-diol 1.6 g of 5% palladized calcium carbonate and 0.6 g of quinoline were added to a solution of 24 g of 2,5-dimethyl-hex-3-yne-2,5-diol [Ray et al, Am. Soc., Vol. 74 (1952), p. 1247] in 200 ml of methanol and the mixture was stirred with hydrogen until hydrogen absorption ceased. The catalyst was removed by filtration and the filtrate was evaporated to dryness under reduced pressure to obtain 24.2 g of cis 2,5-dimethyl-hex-3-ene-2,5-diol melting at 64° C. which was used as is for the next step.

STEP B: Monoacetate of cis 2,5-dimethyl-hex-3-ene-2,5-diol 30 ml of triethylamine and 0.840 g of 4-(N,N-dimethylamino)-pyridine were added to a solution of 10 g of the product of Step A and 10 ml of methylene chloride and the mixture was stirred at room temperature for 4 hours. 7.1 g of acetic acid anhydride were added thereto followed by methylene chloride addition. The organic phase was washed with aqueous 5% hydrochloric acid and then with water, dried and evaporated to dryness under reduced pressure. The 9.6 g of residue were chromatographed over silica gel and were eluted with a 1-25 ether-pentane mixture to obtain after distillation 7.8 g of pure monoacetate of cis 2,5-dimethyl-hex-3-ene-2,5-diol with a boiling point of 60° C. at 0.1 mm Hg.

STEP C: Methyl trans (4-hydroxy-1,1,4-trimethyl-pent-2-enyl)-propanedioate

A solution of the sodium derivative of methyl malonate prepared from 0.48 g of sodium hydride as a 50% oil suspension, 1.5 ml of methyl malonate and 15 ml of anhydrous tetrahydrofuran was added at 70° C. to 4.86 g of the product of Step B and 0.6 g of palladium tetrakistriphenyl phosphine was added thereto. The mixture was stirred at 70° C. for 16 hours and was cooled and poured into water. The mixture was extracted with ether and the organic phase was dried and evaporated to dryness under reduced pressure. The residue was distilled to obtain 2.2 g of methyl trans (4-hydroxy-1,1,4-trimethyl-pent-2-enyl)-propanedioate boiling at 120°-130° C. at 0.01 mm Hg.

EXAMPLE 2

Methyl trans (4-acetyloxy-1,1,4-trimethyl-pent-2-enyl)-propanedioate 2 ml of acetic acid anhydride, 2 ml of triethylamine and 0.084 g of 4-(N,N-dimethylamino)-pyridine were added to a solution of 2 g of the product of Example 1 in 6 ml of methylene chloride and the mixture was stirred at room temperature for 6 hours. The methylene chloride phase was washed with aqueous 5% hydrochloric acid, with an aqueous sodium bicarbonate solution, then with water, dried and evaporated to dryness under reduced pressure. The residue was distilled to obtain 1.98 g of methyl trans (4-acetyloxy-1,1,4-trimethyl-pent-2-enyl)-propanedioate with a boiling point of 100°-110° C. at 0.1 mm Hg.

EXAMPLE 3

Methyl 2,2-dimethyl-3-(2'-methyl-propenyl)-cyclopropane-1,1-dicarboxylate

A mixture of 0.3 g of the product of Example 2, 0.8 ml of tetrahydrofuran, 0.4 ml of hexamethyltriphosphorotriamide and 0.048 g of sodium hydride as a 60% oil suspension was stirred at room temperature for 30 minutes and then a solution of 0.16 g of palladium tetrakistriphenyl phosphine, 0.4 ml of hexamethylphosphorotriamide and 0.8 ml of tetrahydrofuran was added thereto at 70° C. with stirring over 30 minutes. The mixture was stirred for 90 minutes and was poured into water. The mixture was extracted with ether and the organic phase was dried and evaporated to dryness. The residue was chromatographed over silica gel and was eluted with a 1-4 ether-pentane mixture to obtain 0.072 g of methyl 2,2-dimethyl-3-(2'-methyl-propenyl)-cyclopropane-1,1-dicarboxylate.

Various modifications of the products and processes of the invention may be made without departing from the spirit or scope thereof and it is to be understood that the invention is intended to be limited only as defined in the appended claims.

What is claimed is:

1. A penten-2-yl derivative of the formula in the trans form

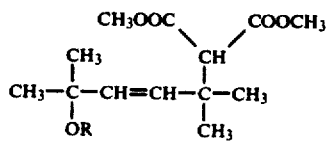
wherein R is selected from the group consisting of hydrogen and acetyl.
2. A compound of claim 1 which is methyl trans (4-hydroxy-1,1,4-trimethyl-pent-2-enyl)-propanedioate.
3. A compound of claim 1 which is methyl trans (4-acetyloxy-1,1,4-trimethyl-pent-2-enyl)-propanedioate.
* * * * *